US00PP27686P3

(12) United States Plant Patent
Trees

(10) Patent No.: US PP27,686 P3
(45) Date of Patent: Feb. 21, 2017

(54) ***IBERIS* PLANT NAMED 'LAVISH'**

(50) Latin Name: *Iberis gibraltarica*
Varietal Denomination: Lavish

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 34 days.

(21) Appl. No.: 14/756,101

(22) Filed: Jul. 31, 2015

(65) Prior Publication Data

US 2016/0066491 P1 Mar. 3, 2016

Related U.S. Application Data

(60) Provisional application No. 62/070,678, filed on Sep. 2, 2014.

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

Trademark Electronic Search System for Lavish retrieved on Oct. 31, 2016, retrieved from the Internet at <http://tmsearch.uspto.gov/bin/showfield?f=doc&state=4801:tn56au.3.1> pp. 1-2.*

* cited by examiner

*Primary Examiner* — June Hwu
(74) *Attorney, Agent, or Firm* — Audrey Charles

(57) ABSTRACT

A new and distinct cultivar of *Iberis* plant named 'Lavish', characterized by its white and light lavender colored flowers, dark green-colored foliage, and moderately vigorous, mounded-spreading growth habit, is disclosed.

1 Drawing Sheet

Latin name of genus and species of plant claimed: *Iberis gibraltarica.*

Variety denomination: 'Lavish'.

BACKGROUND OF THE INVENTION

The present invention relates to a new and distinct cultivar of *Iberis* plant botanically known as *Iberis gibraltarica* and hereinafter referred to by the cultivar name 'Lavish'.

The new cultivar originated in a controlled breeding program in Guadalupe, Calif. during the summer of 2010. The objective of the breeding program was the development *Iberis* cultivars that flower without vernalization and have a long blooming window.

The new *Iberis* cultivar is the result of open-pollination. The female (seed) parent of the new cultivar is the proprietary *Iberis gibraltarica* breeding selection coded NCT-12939-1, not patented, characterized by its white-colored flowers, dark green-colored foliage, and moderately vigorous, mounded-spreading growth habit. The male (pollen) parent of the new cultivar is unknown. The new cultivar was discovered and selected as a single flowering plant within the progeny of the above stated open-pollination during August 2011 in a controlled environment in Guadalupe Grande, Calif.

Asexual reproduction of the new cultivar by terminal stem cuttings since August 2011 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Lavish' as a new and distinct cultivar of *Iberis* plant:

1. White and light lavender colored flowers;
2. Dark green-colored foliage; and
3. Moderately vigorous, mounded-spreading growth habit.

Plants of the new cultivar differ from plants of the female parent primarily in flower color and in continuing to freely flower even under high heat conditions.

Of the many commercially available *Iberis* cultivars, the most similar in comparison to the new cultivar is ABSOLUTELY AMETHYST 'IB2401', U.S. Plant Pat. No. 23,048. However, in side by side comparisons, plants of the new cultivar differ from plants of 'IB2401' in at least the following characteristics:

1. Plants of the new cultivar have smaller flowers than plants of 'IB2401'; and
2. Plants of the new cultivar have a lighter flower color than plants of 'IB2401'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Lavish'. The plants were grown in 1.7 gallon containers for approximately 8 weeks in a greenhouse and 9 weeks outdoors in West Chicago, Ill. Plants were given two pinches prior to transplant.

DETAILED BOTANICAL DESCRIPTION

Figure 1:
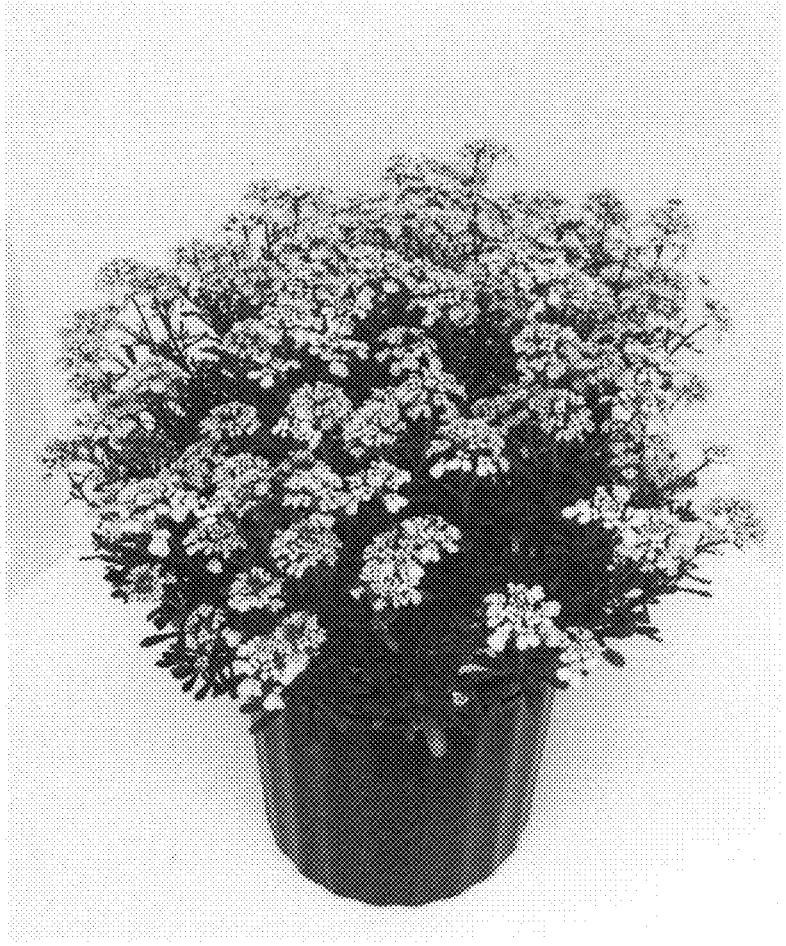
FIG. 1 illustrates a side view of the overall growth and flowering habit of 'Lavish'.
Figure 2:
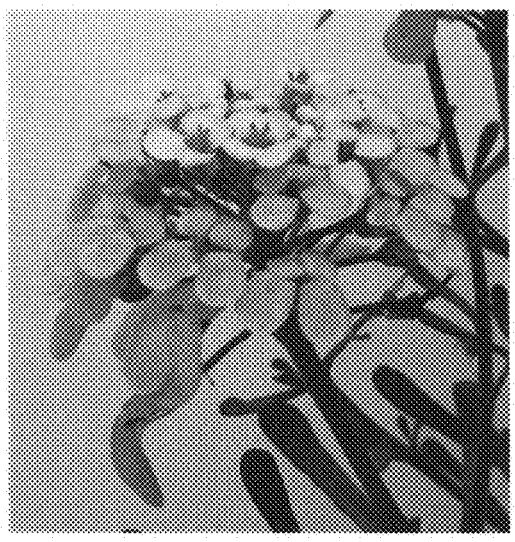
FIG. 2 illustrates a close-up view of the inflorescences of 'Lavish'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in West Chicago, Ill.

The following descriptions and measurements describe plants produced from cuttings from stock plants and grown under conditions comparable to those used in commercial practice. The plants were grown in 1.7 gallon containers for approximately 8 weeks in a greenhouse and 9 weeks outdoors in West Chicago, Ill. Plants were given two pinches prior to transplant. Greenhouse temperatures were maintained at approximately 60° F. to 68° F. (15.5° C. to 20° C.) during the day and approximately 55° F. to 60° F. (13° C. to 15.5° C.) during the night. No supplemental lighting was provided. Measurements and numerical values represent averages of typical plants.

Botanical classification: *Iberis gibraltarica* cultivar Lavish.

Parentage:

*Female parent*.—Proprietary *Iberis gibraltarica* breeding selection coded NCT-12939-1, not patented.

*Male parent*.—Unknown.

Propagation:

*Type cutting*.—Terminal stem.

*Time to initiate roots*.—Approximately 12 to 14 days.

*Time to produce a rooted cutting*.—Approximately 28 to 35 days.

*Root description*.—Fine, fibrous, white in color.

*Rooting habit*.—Freely branching.

Plant description:

*Commercial crop time*.—Approximately 12 to 14 weeks from a rooted cutting to finish in a 15 cm pot.

*Growth habit and general appearance*.—Moderately vigorous, mounded-spreading.

*Size*.—Height from soil level to top of plant plane: Approximately 27.0 cm. Width: Approximately 37.5 cm.

*Hardiness*.—Perennial to USDA Zone 7a 0° F. (−18° C.).

*Heat tolerance*.—Tolerates temperatures as high as 40° F. (4.4° C.) in the summer.

*Branching habit*.—Freely branching. Quantity of main branches per plant: Approximately 7.

*Branch*.—Shape: Ribbed. Strength: Strong. Length: Approximately 19.0 cm. Diameter: Approximately 5.0 mm. Length of central internode: Approximately 6.0 mm. Texture: Ridged and moderately pubescent. Color of young stems: 146C. Color of mature stems: 146C tinted 187A in sun, stems become woody 199B with age.

Foliage description:

*General description*.—Quantity of leaves per main branch: Approximately 21. Fragrance: None detected. Form: Simple. Arrangement: Alternate.

*Leaves*.—Aspect: Perpendicular or acute angle to stem. Shape: Spatulate. Margin: Entire. Apex: Obtuse. Base: Attenuate, sessile. Venation pattern: Pinnate. Length of mature leaf: Approximately 4.2 cm. Width of mature leaf: Approximately 8.0 mm. Texture of upper surface: Moderately pubescent, leathery. Texture of lower surface: Sparsely pubescent. Color of upper surface of young and mature foliage: 137A, venation indistinguishable. Color of lower surface of young and mature foliage: 137C, midvein 146D other venation indistinguishable.

Flowering description:

*Flowering habit*.—'Lavish' is freely flowering under outdoor growing conditions with substantially continuous blooming from early spring through late summer.

*Lastingness of individual flower on the plant*.—Approximately 5 to 7 days.

Inflorescence description:

*General description*.—Type: Corymb. Quantity per plant: Approximately 100. Fragrance: Slight. Length or height of terminal corymb: Approximately 3.0 cm. Width of terminal corymb: Approximately 3.5 cm. Length or height of axillary corymb: Approximately 1.5 cm. Width of axillary corymb: Approximately 3.0 cm. Quantity of fully open flowers per terminal corymb: Approximately 28. Quantity of fully open flowers per axillary corymb: Approximately 14.

*Peduncle*.—Strength: Strong. Aspect: Primary erect, axillary acute angle to stem. Length of primary: Approximately 3.0 cm. Diameter of primary: Approximately 2.0 mm. Length of axillary: Approximately 5.5 cm. Diameter of axillary: Approximately 1.5 mm. Texture: Moderately pubescent. Color: 146B tinted 187A in sun.

Flower description:

*Type*.—Small, asymmetrical cruciferous flowers with two larger abaxial pairs of petals and two smaller adaxial pairs, freely flowering, not persistent, facing outwardly to upright.

*Bud*.—Rate of opening: Generally takes 3 to 4 days for bud to progress from first color to fully open flower.

*Bud just before opening*.—Shape: Globose. Diameter: Approximately 2.0 mm. Color: Sepal centers of 144A tinted with 187A, margins of NN155D with N82B; petals of NN155D.

*Corolla*.—Shape: Cruciform lobes with claws surrounded by calyx. Aspect: Facing upward and outward. Length: Approximately 7.0 mm. Width: Approximately 8.0 mm.

*Petals*.—Quantity: 4. Shape: Obovate. Margin: Entire. Apex: Obtuse. Base: Attenuate. Length of abaxial lobes: Approximately 5.0 mm. Width of abaxial lobes: Approximately 4.0 mm. Length of adaxial lobes: Approximately 2.0 mm. Width of adaxial lobes: Approximately 3.0 mm. Length of claw: Approximately 3.0 mm. Width of claw: Less than 1.0 mm. Color of upper surface of all lobes when first open: NN155D. Color of lower surface of all lobes when first open: NN155D with a faint overlay of N82D. Color of upper surface of all lobes when fully open: N82D. Color of lower surface of all lobes when fully open: NN155D with an overlay of N82D. Color of upper and lower surfaces of claw: NN155D with a midvein of N82D.

*Calyx*.—Shape: Cupped. Diameter: Approximately 5.0 mm.

*Sepals*.—Quantity per flower: 4, distinct. Shape: Ovate. Apex: Obtuse. Base: Truncate. Length: Approximately 4.0 mm. Width: Approximately 2.0 mm. Texture of inner surface: Glabrous. Texture of outer surface: Moderately pubescent. Color of inner and outer surfaces: Centers of 144B tinted with 187A and margins of N82C to N82D.

*Pedicel*.—Strength: Strong, flexible. Aspect: Acute angle to stem. Length: Approximately 8.0 mm. Diameter: Less than 1.0 mm. Texture: Moderately pubescent with adaxial surface densely pubescent. Color: 146B tinted 187A in sun.

*Reproductive organs*.—Androecium: Stamen quantity: 6 per flower. Stamen length: Approximately 4.0 mm, 1 pair slightly shorter and inserted lower. Filament color: 145C with a heavy overlay of 187B. Anther shape: Sagittate, dorsifixed. Anther color: 4A. Pollen amount: Sparse. Pollen color: 4B. Gynoecium: Pistil quantity: 1 per flower, ovary superior, flattened orbicular. Pistil length: Approximately 4.0 mm. Stigma shape: Bifid. Stigma color: 145A. Style length: Approximately 2.0 mm. Style color: 145C with a heavy overlay of 187B. Ovary diameter: Approximately 2.0 mm. Ovary color: N144D.

Seed and fruit production: Neither seed nor fruit production has been observed.

Disease and pest resistance: Resistance to pathogens and pests common to *Iberis* has not been observed.

What is claimed is:

1. A new and distinct cultivar of *Iberis* plant named 'Lavish', substantially as herein illustrated and described.

* * * * *